United States Patent [19]

Kuchar et al.

[11] Patent Number: 4,683,331
[45] Date of Patent: Jul. 28, 1987

[54] OMEGA-(2,4-DIHALOBIPHENYLYL) OXO ALKANOIC ACIDS

[75] Inventors: Miroslav Kuchar; Bohumila Brunova; Jaroslava Grimova; Eva Maturova, all of Prague, Czechoslovakia

[73] Assignee: Spofa spojene podniky pro zdravotnickou, Prague, Czechoslovakia

[21] Appl. No.: 760,338

[22] Filed: Jul. 29, 1985

[30] Foreign Application Priority Data

Aug. 31, 1984 [CS] Czechoslovakia ............ 6586-84

[51] Int. Cl.$^4$ ................................ C07C 59/86
[52] U.S. Cl. ................................ 562/459; 560/51
[58] Field of Search ........................ 562/459

[56] References Cited

U.S. PATENT DOCUMENTS 3,182,061  5/1965  Goldschmidt ............ 562/459

FOREIGN PATENT DOCUMENTS 592074   2/1960  Canada ..................... 562/459
7203400  9/1972  Netherlands ............. 562/459

Primary Examiner—Paul J. Killos

[57] ABSTRACT

The invention relates to omega-(2',4'-dihalobiphenylyl-)oxo alkanoic acids of Formula:

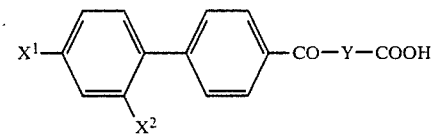

wherein $X^1$ and $X^2$ each represent a fluorine or chlorine atom and Y represents a bivalent hydrocarbon chain selected from the group consisting of —$CH_2$—CH—$CH_3$ and $(CH_2)_3$, and to a process for their preparation.

The compounds of the invention are highly active and longlasting anti-inflammatory agents.

4 Claims, No Drawings

OMEGA-(2,4-DIHALOBIPHENYLYL) OXO ALKANOIC ACIDS

The invention relates to omega-(2',4'-dihalobiphenylyl)oxo alkanoic acids of Formula I:

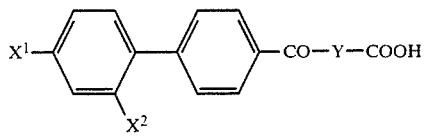

wherein $X^1$ and $X^2$ each represent a fluorine or chlorine atom and Y represents a bivalent hydrocarbon chain selected from the group consisting of —$CH_2$—CH—$CH_3$ and $(CH_2)_3$, and to a process for their preparation.

BACKGROUND OF THE INVENTION

Certain 4-aryl-4-oxo butanoic acids are known to possess anti-inflammatory properties. Belgian Pat. No. 772,804. For example, the compound 4-biphenylyl-4-oxo butanoic acid ("fenbufen") has been used in the treatment of rheumatoid diseases. Similarly, monohalo derivatives of 4-biphenyl-4-oxo-2-methylbutanoic acid demonstrate short-lived anti-inflammatory activity. Swiss Pat. No. 628 014.

In comparison with the unsubstituted parent compound, a monotropoic halogen substitution on the outer aromatic ring of 4-biphenylyl-4-oxo butanoic acid results in a substantial decrease in, or even a total loss of anti-inflammatory action. R. G. Child et al., J. Pharm. Sci. Vol. 66 (1977), pp. 466–76. The reference teaches that the activity of fenbufen for Carrageenin edema is 1.9 and the percent inhibition for adjuvant arthritis is 71%. For 4'-Cl-fenbufen, there is no activity for Carrageenin edema and the percent inhibition for adjuvant arthritis is 61%. For 4'-F-fenbufen, the activity for Carrageenin edema is 1.7 and there is no activity for adjuvant arthritis. See, J. Pharm. Sci., Vol. 66 (1977), pp. 468–9, tabulated at I, II, and XXIX. Thus, the available literature suggests that a ditopic substitution by a chlorine or fluorine atom on the same benzene ring would lead to similar or even greater losses in anti-inflammatory activity.

SUMMARY OF THE INVENTION

The compounds of the invention, such as the 2',4'-dichloro and 2',4'-difluoro embodiments, are highly active anti-inflammatory agents. Both exhibit high levels of activity for both Carrageenin edema and adjuvant arthritis. Thus, the invention discloses that ditopic halogen substitution of the outer aromatic ring of the parent compound, 4-biphenylyl-4-oxo butanoic acid, results in highly active anti-inflammatory compounds that exhibit a significantly prolonged effect by comparison with known compounds. Modification of the aliphatic chain connecting the oxo and carboxyl groups produces a similar result. The new compounds provide potent anti-inflammatory action for more than 24 hours with virtually the same toxicity of the original parent compound.

Particularly active and long-lasting are the embodiments 4-(2',4'-dichlorobiphenylyl)-2-methyl4-oxo butanoic acid and 4-(2',4'-difluorobiphenylyl)-2-methyl4-oxo butanoic acid. The anti-inflammatory activity and short-term toxicity of these two compounds, in comparison with the reference compounds 4-biphenylyl-4-oxo butanoic acid (fenbufen) and 4-(4'-fluorobiphenylyl)-2-methyl-4-oxo butanoic acid are given in Table I. The reference compounds demonstrated a prolonged effect only at doses as high as 100 mg/kg p.o. At substantially lower doses, the anti-inflammatory activity of the inventive compounds lasted far longer than that of the reference compounds.

TABLE I

Pharmacological Evaluation of Acute Toxicity ($LD_{50}$) and Anti-inflammatory Activity of 4-biphenylyl-4-oxo butanoic acid and Derivatives Thereof Anti-inflammatory activity is measured according to Carrageenin edema and Freund adjuvans edema. The assay for Carrageenin edema was performed according to J. Winter, Proc. Soc. Exptl. Biol. Med. Vol. 111 (1962), p 544. Single oral doses are given in the table. Edema size was evaluated 1, 24, and 48 hours after administration of each compound. The assay for Free adjuvans edema was performed according to Z. Horakova and J. Grimova, Ceskosl. Fys. Vol. 17 (1968), p. 137. Single oral doses are given in the table. The edema was evaluated 1, and 24 hours after administration of each compound. All of the tabulated values are statistically significant ($p < 0.05$) except for those given in brackets, [ ].

COMPOUND 1: 4-(2',4'-dichlorobiphenylyl)-2-methyl4-oxo butanoic acid (Example 1)
COMPOUND 2: 4-(2',4'-difluorobiphenylyl)-2-methyl4-oxo butanoic acid (Example 2)
COMPOUND 3: 4-(4'-flourobiphenylyl-2-methyl-4-oxo butanoic acid
COMPOUND 4: 4-biphenylyl-4-oxo butanoic acid (fenbufen)

| COM-POUND | $LD_{50}$ | Dose mg/kg po | Carrageenin % inhibition 1 hr | 24 hr | 48 hr | Dose mg/kg po | Adjuvans % inhibition 1 hr | 24 hr |
|---|---|---|---|---|---|---|---|---|
| 1 | 450 | 25 | 27 | 54 | 58 | 10 | 37 | 38 |
|   |   | 100 | 35 | 73 | 58 | 25 | 40 | 46 |
|   |   |   |   |   |   | 100 | 45 | 55 |
| 2 | 500 | 25 | 30 | 61 | 42 | 25 | 56 | 32 |
|   |   | 100 | 44 | 66 | 45 | 50 | 53 | 46 |
| 3 | 500 | 25 | [16] | 21 | — | 10 | 37 | 31 |
|   |   | 100 | 33 | 34 | — | 20 | 42 | 39 |
| 4 | 600 | 25 | 40 | [14] | — | 10 | 27 | [8] |
|   |   | 100 | 46 | 38 | 0 | 25 | 31 | [9] |
|   |   |   |   |   |   | 100 | 54 | [7] |

The inventive compounds can be prepared in therapeutic dosage forms which contain the active ingredient in combination with known pharmaceutical excipients. The exact dosage administered depends on the patient and the disease, but a general dosage scheme can be developed from the potency data. For oral administration, doses equivalent to or less than that of either reference compound will produce a similar therapeutic effect for a longer period of time.

The present compounds, as shown in Formula I, are advantageously prepared by reacting a 2,4-dihalo biphenyl compound of Formula II,

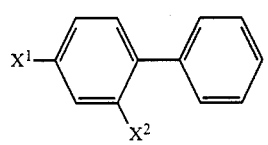

wherein $X^1$ and $X^2$ are as defined in Formula I, with a dicarboxylic anhydride of Formula III,

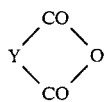

wherein Y is as defined in Formula I. The reaction is conducted in an inert organic solvent, preferably 1,2-dichloroethane, nitromethane, or carbon disulfide, in the presence of a Friedel-Crafts catalyst such as anhydrous aluminum chloride. The reaction temperature may be within the 0° to 50° C. range and is preferably from 10° to 20° C. The starting materials (the compounds of Formulas II and III) can be obtained from known precursors, according to known methods.

The invention is further described with reference to three embodiments thereof. It will be understood by those in the art that these are illustrative examples, and do not serve to limit the scope of the specification and the appended claims.

EXAMPLE 1

4-(2',4'-dichlorobiphenylyl)-2-methyl-4-oxo butanoic acid

A solution is prepared by adding 33.4 g dichlorobiphenyl (0.15 moles) and 18.0 g methylsuccinic acid anhydride (0.15 moles) to 100 ml carbon disulfide. The solution is cooled to 10° C. and is treated portionwise, under stirring, with 24.0 g anhydrous aluminum chloride (0.18 moles) at a rate such that the temperature of the reaction mixture does not exceed 15° C. The mixture is stirred for an additional 4 hours at 20° C. and is then decomposed by pouring into a mixture of 350 ml water and 175 ml concentrated hydrochloric acid. Carbon disulfide is distilled off and the residue is washed with 1,2-dichloroethane (2×100 ml and 1×100 ml). The extracts are combined and washed with a 5% aqueous sodium hydroxide solution (5×75 ml) and water (1×75 ml). The alkaline extracts and aqueous washings are combined, filtered with active carbon, and the clear filtrate is acidified to a strong acid with 50% sulfuric acid. The precipitate is separated, washed with water, and purified by crystallization from 95 ml of 65% acetic acid. The yield is 19.3 g (38.0% of theoretical yield) of the title compound with a melting point of 155°–157° C.

EXAMPLE 2

4-(2',4'-difluorobiphenylyl)-2-methyl-4-oxo butanoic acid

A solution is prepared by dissolving 33.2 g anhydrous aluminum chloride (0.25 moles) and 21.6 g methylsuccinic acid anhydride (0.188 moles) in 190 ml of 1,2-dichloroethane. The solution is cooled to 15° C. and is treated under stirring and cooling with a solution of 47.5 g of 2,4-difluorobiphenyl (0.25 moles) in 50 ml of 1,2-dichloroethane, at a rate such that the temperature of the reaction mixture does not exceed 20° C. The mixture is then stirred for an additional 3 hours at 20° C., for 1 hour at 40° to 45° C., is cooled to 20° C., and is then poured slowly, under stirring, into a mixture of 500 g ice in 250 ml of concentrated hydrochloric acid. The resulting precipitate is collected on a filter, and the organic layer of the filtrate is separated and washed with 5% aqueous sodium hydroxide solution (4×100 ml). The alkaline extracts are combined and the precipitate is dissolved in the extracts. A moderately turbid solution is obtained, which is filtered with active carbon to obtain a clear filtrate. The clear filtrate is acidified to approximately pH 1 with 50% sulfuric acid. The crude product precipitate is separated, washed with water, and purified by crystallization from 160 ml of 65% acetic acid, to yield 24.0 g of the title compound (42% of theoretical yield) with a melting point of 150°–152° C.

EXAMPLE 3

5-(2',4'-difluorobiphenyl)-5-oxo pentanoic acid

In a procedure as set forth in Example 2, using 2,4-difluorobiphenyl and glutaric acid anhydride, the title compound is obtained at 18.5% of theoretical yield after crystallization from 65% acetic acid, with a melting point of 178°–180° C.

We claim:

1. Omega-(2',4'-dihalobiphenylyl)oxo alkanoic acids of the formula

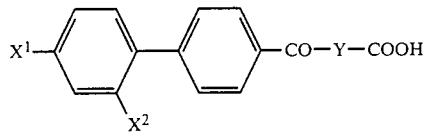

wherein $X^1$ and $X^2$ are each selected from the group consisting of a fluorine atom and a chlorine atom and Y is a bivalent hydrocarbon chain selected from the group consisting of —CH$_2$—CH—CH$_3$ and (CH$_2$)$_3$.

2. 4-(2',4'-difluorobiphenylyl)-2-methyl-4-oxo butanoic acid.

3. 4-(2',4'-dichlorobiphenylyl)-2-methyl-4-oxo butanoic acid.

4. 5-(2',4'-difluorobiphenylyl)-5-oxo pentanoic acid.